United States Patent [19]

Poindexter

[11] 4,381,401
[45] Apr. 26, 1983

[54] AMINOETHYLATION PROCESS

[75] Inventor: Graham S. Poindexter, Evansville, Ind.

[73] Assignee: The Dow Chemical Company, Midland, Mich.

[21] Appl. No.: 309,959

[22] Filed: Oct. 9, 1981

[51] Int. Cl.$^3$ .......................................... C07C 85/00
[52] U.S. Cl. .................................. 556/410; 260/959; 560/19; 560/24; 564/12; 564/52; 564/157; 564/80; 564/413
[58] Field of Search ................ 564/413, 474, 487, 52, 564/157, 80, 12; 556/410; 260/959; 560/24, 19

[56] References Cited

U.S. PATENT DOCUMENTS 2,708,206  5/1955  Girod et al. .................... 564/474 X

FOREIGN PATENT DOCUMENTS 2057744  of 1972  Fed. Rep. of Germany .
 693325  6/1953  United Kingdom ................ 564/487

OTHER PUBLICATIONS

Doklady Akad., Nauk, 59, 489 (1948), (CA 42:6747, 1948).

Primary Examiner—Bernard Helfin
Attorney, Agent, or Firm—Douglas N. Deline

[57] ABSTRACT

2-Oxazolidinone or N-substituted derivatives thereof are reacted with aromatic amine hydrochlorides at elevated temperatures to produce 1,2-ethanediamines.

5 Claims, No Drawings

AMINOETHYLATION PROCESS

BACKGROUND OF THE INVENTION

It is known to produce certain unsymetrically substituted 1,2-ethanediamines. Current processes, however, have proven unacceptable. For example, G. I. Braz et al. disclosed that the aminoethylation of aniline with ethyleneimine afforded only a 13 percent yield of N-phenyl-1,2-ethanediamine. The remaining product comprised polyamino ethyl compounds of high molecular weight. *Dokl. Akad. Nauk.*, 59, 489 (1948), *Chem. Abstr.*, 42, 6747 (1948).

More recently it has been reported that aromatic amine hydrochlorides may be reacted with ethyleneimine to produce the corresponding aromatic aminoethylated adducts, Ger. Offen. No. 2,057,744 (1972). Ethyleneimine, however, is considered very toxic. It would be desirable to provide an improved process for producing aromatic 1,2-ethanediamines. It would be further desirable to provide a process for producing aromatic 1,2-ethanediamine compounds that does not require highly toxic and dangerous reactants.

The 1,2-ethanediamines formed by the present process are an important class of materials which are useful as intermediates for the production of pharmaceuticals, photographic chemicals and other useful compositions. For example, N-(2-(methylphenylamino)ethyl)methanesulfonamide, is a commercially available chemical for use in photographic applications.

SUMMARY OF THE INVENTION

The process described involves the aminoethylation of primary and secondary aromatic amines with one equivalent of 2-oxazolidinone or an N-substituted 2-oxazolidinone. According to the process the aromatic amine or aromatic diamine is first converted to the hydrochloride salt and then reacted by contacting with the desired 2-oxazolidinone or N-substituted derivative thereof at temperatures from about 140° C. to about 190° C. Under these process conditions the 2-oxazolidinone is ring-opened at the 5 position and reacts to yield carbon dioxide and the desired aminoethylated aromatic amine hydrochloride. Neutralization of the hydrochloride salt with base or basic ion-exchange resins affords the free aminoethylated aromatic amine in high yields and purities.

DETAILED DESCRIPTION OF THE INVENTION

The present invention provides an improved process for producing 1,2-ethanediamines of the formula

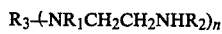

where
n is one or two;
$R_1$ is hydrogen or $C_{1-20}$ hydrocarbyl;
$R_2$ is hydrogen, $C_{1-20}$ alkyl, $C_{1-20}$ hydroxyalkyl, $R_1C(O)-$, $R_1OC(O)-$, $R_1SO_2-$, $(R_1)_3Si-$, $(R_1)_3P$, $(R_1O)_2P(O)-$, or $(R_1O)_3P-$; and
when n is 1, $R_3$ is

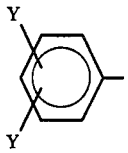

wherein Y independently each occurrence is selected from the group consisting of halogen, amino, $R_1$ and $R_1X-$ where X is oxygen or sulfur; or
when n is 2, $R_3$ is

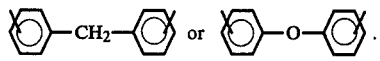

The process employed is the reaction of 2-oxazolidinone or a suitable derivative thereof of the formula

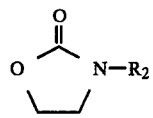

where $R_2$ is as previously defined, with the hydrochloride derivative of an aromatic amine or diamine of the formula

where $R_3$, $R_1$ and n are also as previously defined, followed by neutralization of the hydrogen chloride salt of the desired product.

Of the previously defined substituents, preferred compounds are those wherein n is one and $R_1$ is hydrogen or methyl.

According to the process one needs only to produce the hydrogen chloride salt of the aromatic amine, for example, by reaction with hydrogen chloride and thereafter to contact this salt with 2-oxazolidinone or N-substituted derivatives thereof at elevated temperatures.

Suitably the reactants may be physically contacted as by mechanically mixing or stirring at elevated temperatures optionally in the presence of a suitable solvent such as the well-known $C_{1-10}$ alkanols, $C_{1-10}$ ethers, and $C_{1-4}$ alkyl or phenyl mono- or diethers of alkylene glycols or polyalkylene glycols. Preferred are $C_{1-4}$ alkyl monoethers of polyalkylene glycols. The reactants are combined in about a stoichiometric ratio although more or less of a stoichiometric amount of either reactant may be employed. Suitable temperatures are those from about 140° C. to about 250° C. and preferably from about 160° C. to about 190° C. Use of elevated pressures is not necessary, but may be employed if desired. Preferably no superatmospheric pressure is employed. Generally the reaction is completed in about one to twenty hours and usually in from about two to four hours.

The desired diamine hydrochloride salt is recovered by ordinary techniques. If no solvent is employed, the desired product is readily separated by crystallization upon cooling of the reaction mixture. When a solvent is employed, the product may be recovered by evaporation or similar techniques.

The neutralization is accomplished by contacting the hydrogen chloride salt of the desired amine with a base capable of neutralizing the hydrochloride salt. Examples of suitable bases include aqueous solutions of alkali metal hydroxides or carbonates or a heterogeneous basic ion-exchange resin. An excess of base may be employed to ensure complete neutralization of the hydrogen chloride salt. Suitably from a stoichiometric amount to a ten-fold excess of base may be employed. The neutralization is conducted at ambient conditions and occurs essentially instantaneously.

SPECIFIC EMBODIMENTS

Having described the invention the following examples are provided as further illustrative of the instant invention and are not to be construed as limiting.

EXAMPLE 1

Preparation of N-Phenyl-1,2-ethanediamine

A mixture of aniline hydrochloride (13.5 g, 0.10 mole) and 2-oxazolidinone (9.0 g, 0.10 mole) in 35 ml of 2-(2-methoxyethoxy)ethanol was allowed to stir at 170° C. in an oil bath during which time carbon dioxide gas evolution occurred. After approximately four hours, the gas evolution had ceased and the dark reaction solution was allowed to cool to room temperature. Most of the solvent was removed by rotary-evaporation (95° C./10 mm Hg water pressure) to give a dark solid residue. This residue was taken up in 100 ml of a 10 percent aqueous sodium hydroxide solution and extracted with three portions of chloroform. The combined chloroform extractions were then dried over anhydrous potassium carbonate. After filtration, the chloroform was removed in vacuo to afford 20.4 g of the crude diamine as a greenish brown liquid (97 percent crude yield). Distillation at 93° C. to 100° C. (0.4 mm Hg) gave a 71 percent purified yield of the diamine as a clear liquid. Spectral data confirmed the structure of N-phenyl-1,2-ethanediamine as compared to an authentic specimen.

EXAMPLE 2

Preparation of N-Methyl-N-phenyl-1,2-ethanediamine

In a procedure similar to Example 1, N-methylaniline hydrochloride (17.4 g, 0.10 mole), 2-oxazolidinone (8.7 g, 0.10 mole) and 50 ml of 2-(2-methoxyethoxy)-ethanol were heated for four hours. Removal of the solvent in vacuo gave a quantitative yield of N-methyl-N-phenyl-1,2-ethanediamine hydrochloride as a purplish solid. Workup as before afforded the crude diamine in also a quantitative crude yield as a dark yellow liquid. Distillation at 95° C. to 100° C. (0.5 mm Hg) gave a 79 percent yield of the purified product as a clear liquid. Spectral data and gas chromatographic analysis as compared to an authentic sample confirmed its structure.

EXAMPLE 3

Preparation of N-Methyl-N'-phenyl-1,2-ethanediamine

A mixture of aniline hydrochloride (13.0 g, 0.10 mole), 3-methyl-2-oxazolidinone (11.0 g, 0.109 mole) and 35 ml of 2-(2-methoxyethoxy)ethanol was heated to 170° C. in an oil bath. The reaction mixture became homogenous and carbon dioxide evolution occurred on heating. After 17 hours, the reaction was allowed to cool to room temperature. After a workup procedure similar to that described in Example 1 and distillation at 105° C. to 110° C. (0.4 mm), an 81 percent distilled yield of the product was obtained as a clear liquid. Product confirmation was made by the use of spectra evidence.

EXAMPLE 4

Preparation of N-(2-Hydroxyethyl)-N'-phenyl-1,2-ethanediamine

A mixture of aniline hydrochloride (19.5 g, 0.15 mole), 3-(2-hydroxyethyl)-2-oxazolidinone (20.6 g, 0.157 mole) and 50 ml of 2-(2-methoxyethoxy)ethanol was heated to 168° C. for 16 hours. The orange solution was cooled to room temperature and worked up in a procedure similar to that cited in Example 1. Kugelrohr distillation at 150° C. to 160° C. (0.2 to 0.3 mm) gave a 67 percent yield of the material as a pale yellow oil. Spectral evidence confirmed its structure.

EXAMPLE 5

Preparation of Ethyl(2-(phenylamino)ethyl)carbamate

A mixture of aniline hydrochloride (8.7 g, 66.9 mmole), N-carboethoxy-2-oxazolidinone (10.1 g, 63.5 mmole) and 25 ml of 2-(2-methoxyethoxy)ethanol was heated to 160° C. Gas evolution began occurring at 140° C. and continued for 3 hours. The dark homogenous reaction solution was allowed to cool to ambient temperature and worked up according to the procedure described in Example 1. Distillation at 170° C. (0.5 mm) gave a 26 percent yield of a clear oil which slowly solidified on standing.

EXAMPLE 6

Preparation of Ethyl 4[N-(2-aminoethyl)]aminobenzoate

In a manner similar to the above two examples, ethyl p-aminobenzoate hydrochloride (21.7 g, 0.11 mole), 2-oxazolidinone (8.8 g, 0.10 mole) and 50 ml of 2-(2-methoxyethoxy)ethanol was heated to 175° C. for two hours. Removal of solvent and workup gave 23.1 g of the crude product as a dark yellow liquid. Kugelrohr distillation (bulb to bulb) at 130° C. to 160° C. (oven temperature) (0.1 mm Hg) afforded a 61 percent yield of the diamine as a clear liquid which slowly solidified on standing at ambient temperatures to a white waxy solid. Spectral evidence confirmed its structure.

EXAMPLE 7

Preparation of N-(4-aminophenyl)-1,2-ethanediamine

A mixture of p-diaminobenzene dihydrochloride (20.1 g, 0.11 mole), 2-oxazolidinone (17.4 g, 0.20 mole) and 100 ml of 2-(2-methoxyethoxy)ethanol was heated to 189° C. in an oil bath while being vigorously stirred mechanically. After two and one-half hours, all gas evolution had ceased and the dark purple reaction mixture was allowed to cool to room temperature. Most of the solvent was removed in vacuo while applying heat (95° C./10 mm Hg) to give a viscous, dark purple oil. After dissolution of the crude triamine dihydrochloride in 100 ml of a 10 percent aqueous sodium hydroxide solution, the free amine was extracted with three portions of chloroform. During the extraction, solid sodium chloride was added to help break up the emulsion which formed. The combined chloroform portions were dried over anhydrous potassium carbonate and filtered. After removal of the solvent in vacuo, approximately 20 g of the crude amine was obtained as a dark yellow oil. Kugelrohr distillation (bulb to bulb) at 160° C. to 190° C. (0.1 mm Hg) afforded a 29 percent yield of the triamine as a pale yellow oil. The product structure was confirmed by spectral studies.

EXAMPLE 8

Preparation of N-(2-Chlorophenyl)-1,2-ethanediamine

A mixture of 2-chloroaniline hydrochloride (17.1 g, 0.105 mole), 2-oxazolidinone (8.7 g, 0.10 mole) and 40 ml of 2-(2-methoxyethoxy)ethanol was heated to 170° C. in an oil bath for five hours. From time to time, a colorless material which formed on the sides of the reaction flask was scraped off into the reaction mixture. On cooling, a white amorphous material solidified. Filtration afforded the crude ethanediamine hydrochloride. Neutralization similar to that described in Example 1 and distillation at 90° C. (0.5 mm Hg) gave a 50 percent yield of the product.

EXAMPLE 9

Preparation of N-(4-Methoxyphenyl)-1,2-ethanediamine

A mixture of 4-methoxyaniline hydrochloride (17.1 g, 0.107 mole), 2-oxazolidinone (8.7 g, 0.10 mole) and 50 ml of 2-(2-methoxyethoxy)ethanol was heated to 175° C. After five hours, carbon dioxide gas evolution had ceased and the dark mixture was allowed to cool to room temperature. Neutralization in a manner similar to that described in Example 1, and distillation at 130° C. to 140° C. (0.5 mm Hg) afforded a 45 percent yield of the amine as a colorless liquid which slowly solidified on standing at ambient temperature to a low-melting solid.

EXAMPLE 10

Preparation of N-(4-Methylphenyl)-1,2-ethanediamine

A mixture of 4-methylaniline hydrochloride (15.0 g, 0.10 mole), 2-oxazolidinone (8.7 g, 0.10 mole) and 40 ml of 2-(2-methoxyethoxy)ethanol was heated in an oil bath to 170° C. for four hours. On cooling to room temperature, a solid formed. Workup as described in Examples 1 and 8, followed by distillation at 110° C. to 120° C. (1.5 mm Hg) gave a 76 percent yield of the material as a clear liquid which slowly solidified on standing at ambient temperatures to a low-melting solid.

EXAMPLE 11

Preparation of N,N''-(Oxydi-4,1-phenylene)bis(1,2-ethanediamine)

In a procedure similar to Example 1, a mixture of 4,4'-diaminodiphenyl ether dihydrochloride (27.3 g, 0.10 mole), 2-oxazolidinone (17.4 g, 0.20 mole) and 100 ml of 2-(2-methoxyethoxy)ethanol was heated to 190° C. while stirring mechanically. After five hours, all gas evolution had ceased and the dark reaction mixture was cooled to room temperature. Workup as described above afforded 38.6 g of the crude tetraamine as a dark brown oil. Kugelrohr distillation at 170° C. to 250° C. (0.1 mm Hg) gave a 55 percent yield of the product as a pale yellow, viscous oil which very slowly solidified on standing at room temperature to a yellow solid. As before, spectral evidence confirmed its structure.

EXAMPLE 12

Preparation of N,N''-(Methylenedi-4,1-phenylene)bis(1,2-ethanediamine)

A mixture of 4,4'-methylenedianiline dihydrochloride (135 g, 0.50 mole), 2-oxazolidinone (91.0 g, 1.05 mole) and 300 ml of 2-(2-methoxyethoxy)ethanol was heated to 168° C. in an oil bath where carbon dioxide evolution occurred. After five hours, the dark yellow mixture was cooled to ambient temperature. The reaction product was neutralized by the addition of 200 ml of 20 percent aqueous sodium hydroxide solution. After separation of phases, the aqueous phase was extracted with 2-(2-methoxyethoxy)ethanol and dried over anhydrous sodium sulfate. After filtration the mixture was distilled at 135° C. to 250° C. (0.1 mm Hg) to give a 48 percent yield of the tetraamine as a viscous yellow oil. Spectral data confirmed its structure.

EXAMPLE 13

Preparation of N-(3-Chlorophenyl)-1,2-ethanediamine

Gaseous hydrogen chloride was reacted with m-chloroaniline in ether at 0° C. to prepare the m-chloroaniline hydrochloride. This reactant (65.6 g, 0.4 mole) was then intimately mixed with 2-oxazolidinone by grinding with a mortar and pestle. The ground mixture was then added to a 250 ml flask equipped with a mechanical stirrer and gas vent. The flask was heated in an oil bath to 160° C. with stirring. The solid mixture melted and $CO_2$ evolution commenced in about 15 minutes. Heating was continued for about six hours whereupon the flask was cooled and the contents dissolved in water and filtered. The filtrate was then basified with aqueous caustic causing a yellow oil to separate. Extraction with methylene chloride, drying and distillation under vacuum gave 55 g (80 percent yield) of N-(3-chlorophenyl)-1,2-ethanediamine.

What is claimed is:

1. A process for preparing 1,2-ethanediamines of the formula

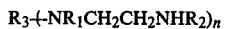

where n is one or two;

$R_1$ is hydrogen or $C_{1-20}$ hydrocarbyl;

$R_2$ is hydrogen, $C_{1-20}$ alkyl, $C_{1-20}$ hydroxyalkyl, $R_1C(O)-$, $R_1OC(O)-$, $R_1SO_2-$, $(R_1)_3Si-$, $(R_1)_3P$, $(R_1O)_2P(O)-$, or $(R_1O)_3P-$; and when n is 1, then $R_3$ is

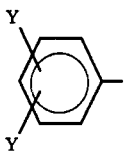

wherein Y independently each occurrence is selected from the group consisting of halogen, amino, $R_1$ and $R_1X-$ where X is oxygen or sulfur; and when n is 2, then $R_3$ is:

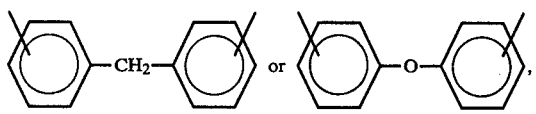

comprising contacting 2-oxazolidinone or a derivative thereof having the formula

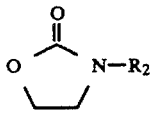

where $R_2$ is as previously defined, with the hydrochloride derivative of an aromatic amine or diamine of the formula:

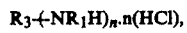

where n, $R_1$ and $R_3$ are as previously defined, at a temperature of from about 140° C. to about 250° C. for a time sufficient to form substantial amounts of the corresponding 1,2-ethanediamine hydrochloride salt and thereafter contacting with base.

2. The process of claim 1 wherein 2-oxazolidinone or a derivative thereof and the hydrochloride derivative of an aromatic amine or diamine are contacted at a temperature from about 160° C. to about 190° C.

3. The process of claim 1 or 2 wherein 2-oxazolidinone or a derivative thereof and the hydrochloride derivative of an aromatic amine or diamine are contacted in a solvent selected from $C_{1-10}$ alkanols, $C_{1-2}$ alkyl ethers and phenyl or $C_{1-4}$ alkyl mono- or diethers of alkylene and polyalkylene glycols.

4. The process of claim 3 wherein the solvent is a $C_{1-4}$ alkyl monoether of polyalkylene glycols.

5. The process of claim 1 wherein the base is aqueous alkali metal hydroxide.

* * * * *